(12) United States Patent
Sharpe (10) Patent No.: US 7,498,168 B2
(45) Date of Patent: Mar. 3, 2009

(54) TOOTH PROGENITOR CELL AND METHOD FOR ITS PRODUCTION

(75) Inventor: Paul Thomas Sharpe, London (GB)

(73) Assignee: Odontis Limited, London (GB)

( * ) Notice: Subject to any disclaimer, the term of this patent is extended or adjusted under 35 U.S.C. 154(b) by 318 days.

(21) Appl. No.: 10/204,208

(22) PCT Filed: Feb. 16, 2001

(86) PCT No.: PCT/GB01/00651

§ 371 (c)(1),
(2), (4) Date: Oct. 30, 2002

(87) PCT Pub. No.: WO01/60981

PCT Pub. Date: Aug. 23, 2001

(65) Prior Publication Data

US 2003/0103950 A1 Jun. 5, 2003

(30) Foreign Application Priority Data

Feb. 18, 2000 (GB) ................................ 0003930.5

(51) Int. Cl.
*C12N 5/00* (2006.01)
*C12N 5/02* (2006.01)
*C12N 5/08* (2006.01)
*C12N 5/06* (2006.01)
*C12N 5/10* (2006.01)

(52) U.S. Cl. ........................ 435/373; 435/366; 435/368; 435/371; 435/377; 435/354

(58) Field of Classification Search ................ 435/325, 435/366, 374, 404, 405, 395, 401, 373, 368, 435/371, 377, 354
See application file for complete search history.

(56) References Cited

FOREIGN PATENT DOCUMENTS

EP 1259593 B1 8/2001

OTHER PUBLICATIONS

Quint et al. J.. of Exp. Zoology, 288:235-241 (2000).*
Ohkubo et al. Neuroscience, 111(1): 1-17 (2002).*
Sharpe et al. Sci. Amer., 293 (2): 34-41 (Aug. 2005).*
Fong et al. J. Dent. Educ., 69:555-570 (2005).*
Verfaillie et al. Hematology (Am Soc Hematol Educ Program). 2002;:369-91.*
Baba et al. Archs. Oral Biol., 41(2): 215-219 (1996).*
Thomas et al. Arch. Oral Biol., 34(1): 27-35 (1989).*
Masella et al. Am. J. Orthod. Dentofacial. Orthop., 129: 458-68, 2006.*
Vale et al, "the Inhibin/Activin Family of Hormones and Growth Factors," Peptide Growth Factors and Their Receptors II Chapter 26, Springer Verlag Berlin, Germany, 1990.
Trowell, O.A., "The Culture of Mature Organs in a Synthetic Medium," Experimental Cell Research 16, p. 118-147, 1959.
Teixeira, Cristina, "New Horizons in Understanding Early Tooth development," Clin. Orthod. Res. 2, 1999, pp. 171-174.
Asashime et al, "Mesodermal induction in early amphibian embryos by activin A (erthroid differentiation factor)" Roux's Archives of Developmental Biology 198; 1990, pp. 330-335.
Saxen, Lauri. "Effect of Tetracycline on Osteogenesis in Vitro," J. Exp. Zool. 162; pp. 269-294.
Wilkinson, David, "Whole Mount in Situ Hybridization of Vertebrate Embryos," In situ Hybridization, A Practical Approach Chapter 6, IRL Press, Oxford, UK, 1995.
Kollar et al., "The Influence of the Dental Papilla on the Development of Tooth Shape in Embryonic Mouse Tooth Germs," J. Embryol. Exp. Morph. vol. 21, Feb. 1969, pp. 131-148.
Mina et al, "The Induction of Odontogenesis in Non-Dental Mesenchyme Combined with Early Murine Mandibular Arch Epithelium," Archs Oral Biol., vol. 32, No. 2, 1987, pp. 123-127.
Lumsden, A.G.S., "Spatial Organization of the Epithelium and the Role of Neural Crest cells in the Initiation of the Mammalian Tooth Germ," Development 103 Supplement, 1988, pp. 155-169.
Nakamura et al., "Activin-Binding Protein from Rat Ovary is Follistatin," Science vol. 247, Feb. 1990, pp. 836-838.
Green et al, "Graded Changes in Dose of a *Xenopus* Activin A Homologue Elicit Stepwise Transitions in Embryonic Cell Fate," Nature vol. 347, Sep. 1990, pp. 391-394.
Thomsen et al, "Activins are Expressed Early in *Xenopus* Embryogenesis an Can Include Axial Mesoderm and Anterior Structures," Cell vol. 63, Nov. 2, 1990, pp. 485-493.
Roberts et al, "Expression of Inhibin/Activin Subunit Messenger Ribonucleic Acids during Rat Embryogenesis," Endocrinology vol. 128, No. 6, 1991, pp. 3122-3129.
Mackenzie et al, "The Homeobox Gene Hox 7.1 has Specific Regional and Temporal Expression Patterns During Early Murine Craniofacial Embryogenesis, Especially Tooth Development in Vivo and in vitro," Development 111, 1991, pp. 269-285.
Vaahtokari et al, "Associations between transforming Growth Factor B1 RNA Expression and Epithelial—mesenchymal Interactions During Tooth Morphogenesis," Development 113, 1991, pp. 985-994.
Hemmati-Brivanlou et al, "A Truncated Activin Receptor Inhibits Mesoderm Induction and Formation of Axial Structures in *Xenopus* Embryos," Nature vol. 359, Oct. 15, 1992, pp. 609-614.

(Continued)

*Primary Examiner*—Thaian N Ton
(74) *Attorney, Agent, or Firm*—Fulbright & Jaworski LLP (57) ABSTRACT

The invention relates to the use of a cultured stem cell to produce a tooth progenitor cell.

5 Claims, 2 Drawing Sheets

OTHER PUBLICATIONS

Green et al, "Responses of Embryonic *Xenopus* Cells to Activin and FGF are seperated by Multple Dose Thresholds and Correspond to Distinct Axes of the Mesoderm," Cell vol. 71, Nov. 27, 1992, pp. 731-739.

Dohrmann et al, "Expression of Activin mRNA during Early Development in *Xenopus laevis*," Developmental Biology 157, 1993, pp. 474-483.

Michel et al, "Follistatins: More than Follicle-Stimulating Hormone Supressing Proteins," Molecular and Cellular Endocrinology 91, 1993, pp. 1-11.

Vainio et al, "Identification of BMP-4 as a Signal Mediating Secdondary Induction between Epithelial and Mesenchymal Tissues during Early Tooth Develpoment," Cell vol. 75, Oct. 8, 1993, pp. 45-58.

Hemmati-Brivanlou et al, "Inhibition of Activin Receptor Signaling Promotes Neuralization in *Xenopus*," Cell, Feb. 24, 1994, pp. 273-281.

Satokata et al, "Msx1 Deficient Mice Exhibit Cleft Palate and Abnormalities of Craniofacial and Tooth Development," Nature Genetics vol. 6, Apr. 1994, pp. 348-355.

Conlon et al, "A Primary Requirement for Nodal in the Formation and Maintenance of the Primitive Streak in the Mouse," Development 120, 1994, pp. 1919-1928.

Hemmati-Brivanlou et al, "Follistatin, an Antagonist of Activin, is expressed in the Spemann Organizer and Dsiplays Direct Neuralizing Activity," Cell Feb. 24, 1994, pp. 283-295.

Heikinheimo et al, "Fgf-8 Expression in the Post-Grastrulation Mouse Suggests roles in the Development of the Face, Limbs, and Central Nerous System," Mechanisms of Development 48 48, 1994, pp. 129-138.

Roberts et al, "Expression of Messenger Ribonucleic Acids Encoding the Inhibin/Activin System during Mid-and Late-Gestation Rat Embryogenesis," Endocrinology vol. 134, No. 2, 1994, pp. 914-923.

Feijen et al, "Expression of activin Subunits, Activin Receptors and Follistatin in Postimplantation Mouse Embryos Suggests Specific developmental Functions for Different activins," Development 120, 1994, pp. 3621-3637.

Chai et al, "Specific Transforming Growth Factor-B Subtypes Regulate Embryonic Mouse Meckel's Cartilage and tooth Development," Developmental Biology 162, 1994, pp. 85-103.

van Genderen et al, "Development of Several Organs that Require Inductive Epithelial-mesenchymal Interactions is Impaired in LEF-1-deficient Mice," Genes & Development 8, 1994, pp. 2691-2703.

Matzuk et al, "Functional Analysis of Activins During Mammalian Development," Nature vol. 374, Mar. 23, 2995, pp. 354-356.

Matzuk et al, "Different Phenotypes for Mice Deficient in Either Activins or Activin Receptor Type II," Nature vol. 374, Mar. 23, 1995, pp. 356-360.

Tissier-Seta et al, "Barx1, a New Mouse Homeodomain Transcription Factor Expressed in cranio-Facial Ectomesenchyme and the Stomach," Mechanisms of Development 51, 1995, pp. 3-15.

Thesleff et al, "Regulation of Organogenesis. Common Molecular Mechanisms Regulating the Development of Teeth and Other Organs," Int. J. Dev. Biol. 39, 1995, pp. 35-50.

Thomas et al, "The Spatial Localization of Dix-2 During Tooth Development," Connective Tissue Research vol. 32, No. 1-4, 1995, pp. 27-34.

Yamashita et al, "Osteogenic Protein-1 Binds to Activin Type II Receptors and induces Certain Activin-like Effects," The Journal of Cell biology, vol. 130, 1995, pp. 217-226.

Bitgood et al, "Hedgehog anf Bmp Genes Are Coexpressed at Many Diverse Sites of Cell-Cell Interaction in th Mouse Embryo," developmental Biology 172, 1995, pp. 126-138.

Crossley et al, "The Mouse Fgf8 Gene Encodes a Family of Polypeptides and is Expressed in Regions that Direct Outgrowth and Patterning in the Developing Embryo," Developmental 121, 1995, pp. 439-451.

Semina et al, "Cloning and Characterization of a Novel Bicoid-related Homeobox Transcription Factor Gene, RIEG, involved in Rieger Syndrome," Nature Genetics vol. 14, Dec. 1996, pp. 392-399.

Iseki et al, "Sonic Hedgehog is Expressed in Epithelial Cells During Developmental of Whisker, Hair and Tooth," Biochemical and Biophysical Research Communications 218, 1996, pp. 688-693.

Pownall et al, "eFgF, Xcad3 and Hox genes form a molecular Pathway that Establishes the Anteroposterior Axis in *Xenopus*," Development 122, 1996, pp. 3881-3892.

Kratochwil et al, "Lef1 Expression is Activated by BMP-4 and Regulates Inductive Tissue Interactions in Tooth and Hair Development," Genes & Development 10, 1996, pp. 1382-1394.

Bagutti et al, "Differentiation of Embryonal Stem Cells into Keratinocytes: Comparison of Wild-Type and B1 Intergrin-Deficient Cells," Developmental Biology 179, 1996, pp. 184-196.

de Winter et al, "Follistatins Neutralize Activin Bioactivity by Inhibition of Activin Binding to its type II Receptors," Molecular and Cellular Endocrinology 116, 1996, pp. 105-114.

Vaahtokari et al, "The Enamel Knot as a Signaling Center in the Developing Mouse Tooth," Mechanisms of Development 54, 1996, pp. 39-43.

Chen et al, "Msx1 Controls Inductive Signaling in Mammalian Tooth Morphogenesis," Developmental 122, 1996, pp. 3035-3044.

Heikinheimo et al, "The Activin-binding Protein Follistatin is Expressed in Developing Murine Molar and Induces Odontoblast-like Cell Differentiation in vitro," J. Dent Res 76 (10), Oct. 1997, pp. 1625-1636.

Mucchielli et al, "Mouse Otlxt2/RIEG Expression in the Odontogenic Epithelium Precedes Tooth Initiation and Requires Mesenchyme-Derived Signals for Its Maintenance," Developmental Biology 189, 1997, pp. 275-284.

Qiu et al, "Role of the Dlx Hoeobox Genes in Proximodistal Patterning of the Branchial Arches: Mutations of Dlx-1, Dlx-2 and Dlx-1 and -2 Alter Morphogenesis of Proximal Skeletal and Soft Tissue Structures Derived from the First and Second Arches," Developmental Biology 185, 1997, pp. 165-184.

Neubuser et al, "Antagonistic Interactions between FGF and BMP Signaling Pathways: A Mechanism for Positioning the Sites of Tooth Formation," Cell vol. 90, Jul. 25, 1997, pp. 247-255.

Dyson et al, "Activin Signaling has a Necessary Function in *Xenopus* Early development," Current Biology 7, 1997, pp. 81-84.

Thesleff et al, "Signalling Networks Regulating Dental Development," Mechanisms of Development 67, 1997, pp. 111-123.

Thomas et al, Role of Dlx-1 and Dlx-2 Genes in Patterning of the Murine Dentition, Development 124, 1997, pp. 4811-4818.

Aberg et al, "Expression Patterns of Bone Morphogenetic Proteins (Bmps) in the Developing Mouse Tooth Suggest Roles in Morphogenesis and Cell Differentiation," Developmental Dynamics 210, 1997, pp. 383-396.

Fainsod et al, "The Dorsalizing and Neural Inducing Gene Follistatin is an Antagonist of BMP-4," Mechanism of Development 63, 1997, pp. 39-50.

Ferguson et al, "Activin is an Essential Early Mesenchymal Signal in Tooth Development that is Required for Patterning of the Murine Dentition," Genes & Development 12, 1998, pp. 2636-2649.

Kettunen et al, "Expression and Function of FGFs -4,-8, and -9 Suggest Functional Redundancy and Repetitive Use as Epithelial Signals During Tooth Morphogenesis," developmental Dynamics 211, 1998, pp. 256-268.

Hardcastle et al, "The Shh Signaling Pathway in Tooth Development: Defects in GLi2 and Gli3 Mutants," Development 125, 1998, pp. 2803-2811.

Grigoriou et al, "Expression and Regulation of Lhx6 and Lhx7, a novel subfamily of LIM Homedomain Encoding Genes, Suggests a Role in Mammalian Head Development," Development 125, 1998, pp. 2063-2074.

Tucker et al, "Transformation of Tooth Type Induced by Inhibition of BMP Signaling," Science vol. 282, Nov. 6, 1998, pp. 1136-1138.

Thesleff et al, "Molecular Regulation of Tooth Development," Bone vol. 25, No. 1, Jul. 1999, pp. 123-125.

Gage et al, "Dosage Requirement of Pitx2 for Development of Multiple Organs," Development 126, 1999, pp. 4643-4651.

Rathjen et al, "Formation of a Primitive Ectoderm like Cell Population, EPL cells, from ES Cells in reponse to Biologically Derived Factors," Journal of Cell Science 112, 1999, pp. 601-612.

Lin et al, "Pitx2 Regulates Lung Asymmetry, Cardiac Positioning and Pituitary and Tooth Morphogenesis," Nature vol. 401, Sep. 16, 1999, pp. 279-282.

Lu et al, "Function of Rieger Syndrome Gene in Left-Right Asymmetry and Craniofacial Development," Nature vol. 401, Sep. 16, 1999, pp. 276-278.

Sarkar et al, "Inhibition of Wnt Signaling by Exogenous Mfrzb1 Protein Affects Molar Tooth Size," Journal of Dental research vol. 79, No. 4, 2000, pp. 920-925.

Thesleff, Irma, "Genetic Basis of Tooth Development and Dental Defects," Acta Odontol Scand 58, 2000, pp. 191-194.

Ferguson et al, "Temporospatial Cell Interactions Regulating Mandibular and Maxillary Arch Patterning," Development 127, 2000, pp. 403-412.

Matzuk et al, "Multiple Defects and Perinatal Death in Mice Deficient in Follistatin," Nature Nol. 374, Mar. 23, 1995, pp. 360-363.

Heiko Peters, Annette Neubüser, Klaus Kratochwil and Rudi Balling, Pax9-deficient mice lack pharyngeal pouch derivatives and teeth and exhibit craniofacial and limb abnormalities, Genes & Dev. (1998) 12: 2735-2747.

Linden GJ. Bone induction in implants of decalcified bone and dentine. J Anat. Apr. 1975;119(Pt 2):359-67.

Morio I. Recombinant study of the mouse molar cervical loop and dental papilla by renal transplantation. Arch Oral Biol. 1985;30(7):557-61. (PubMed Abstract).

Acampora, D., et al., Craniofacial, vestibular and bone defects in mice lacking the Distal-less related gene Dlx5, Development (1999) 126, 3795-3809.

* cited by examiner

TOOTH PROGENITOR CELL AND METHOD FOR ITS PRODUCTION

FIELD OF THE INVENTION

The invention relates to the production of a tooth progenitor cell. In particular, the invention relates to the use of a cultured stem cell to produce a tooth progenitor cell.

BACKGROUND TO THE INVENTION

Teeth are essential organs for animal survival and of obvious clinical and/or cosmetic importance. There are many instances where tooth replacement is desirable and current treatments are restricted to artificial prostheses or implants.

Tooth primordia explants can be cultured in vitro allowing a variety of manipulation studies including introduction of genes and/or proteins and tissue recombinations. Manipulated primordia can be transferred to renal capsules of adult animals (such as mice) to produce conditions for development of adult teeth. However, these culture techniques require frequent animal sacrifice. This is one of the problems associated with the prior art.

Prior art approaches to the production of tooth primordia relied on in vitro tissue recombination. Two different tissue types were independently dissected from the animal embryo, and these were recombined in the laboratory. Signals from one may then induce formation of tooth primordia in the other. This is a labour intensive process carried out by highly trained workers involving a great deal of surgical skill.

According to the prior art, the tissue requirements for progression of tooth development change early in development. For initiation, it is thought that oral epithelium is essential and can form teeth when recombined with any mesenchymal cells, as long as they are derived from the neural crest. Thus, according to the prior art, neural crest derived cells are essential for the formation of tooth progenitor cells.

The present invention seeks to overcome at least some of the problems associated with the prior art.

SUMMARY OF THE INVENTION

As explained above, production of tooth primordia has only previously been accomplished using tissue recombination techniques. It is surprisingly shown herein that production of tooth progenitor cells may be accomplished using cells cultured in the laboratory. In particular, tooth progenitor cells may be produced using embryonic stem cells (ES cells) cultured in the laboratory.

Accordingly, the present invention provides for the use of a cultured cell to produce a tooth progenitor cell. Preferably, the cultured cell is a stem cell. More preferably, the cultured cell is an ES cell.

The production of tooth progenitor cells from cultured stem cells may advantageously be accomplished by inducing said ES cells with oral epithelium.

A tooth progenitor cell is one which expresses certain molecular markers characteristic of tooth progenitor cells. For example, a cell would be considered to be a tooth progenitor cell if it expressed one or more tooth mesenchymal cell markers. Examples of such markers include Barx1, Dlx2, Dlx5, Msx1, Pax9, Activin βA, Lhx6, Lhx7 and others. These markers may be detected by any suitable means, such as western blotting, immunofluorescence, radioactive in situ hybridisation or other suitable means, which are described in more detail below.

Oral epithelium may be from any suitable source, such as from a mouse. The preparation of oral epithelium is discussed in more detail below.

DETAILED DESCRIPTION OF THE INVENTION

According to a first aspect, the invention relates to use of a cultured cell to produce a tooth progenitor cell.

According to a second aspect, the invention relates to use of a cultured cell to produce a tooth progenitor cell, wherein said cultured cell is a stem cell. The cultured stem cell may be a neural stem cell (NSC), or an embryonic stem cell (ES cell). Preferably, said cultured cell is an embryonic stem cell (ES cell).

According to a third aspect, the invention relates to a method for production of a tooth progenitor cell from a cultured cell, said method comprising; providing a cultured cell, contacting the cultured cell with one or more oral epithelial cells, and incubating for a time sufficient to produce said tooth progenitor cell.

According to a fourth aspect, the invention relates to a method for production of a tooth progenitor cell from a cultured cell, wherein the cultured cell is an ES cell, said method comprising; providing a cultured ES cell, contacting the cultured ES cell with one or more oral epithelial cells, and incubating for a time sufficient to produce said tooth progenitor cell.

According to a fifth aspect, the invention relates to a tooth progenitor cell produced from a cultured cell.

According to a sixth aspect, the invention relates to a tooth progenitor cell produced from a cultured cell wherein said cultured cell is an ES cell.

For ease of reference, these and further aspects of the present invention are now discussed under appropriate section headings. However, the teachings under each section are not necessarily limited to each particular section.

Preferable Features

Preferably, the cultured cell is a stem cell. More preferably, the cultured cell is an ES cell.

Incubation of the cultured ES cell with the epithelial cell(s) is for a time sufficient to produce the tooth progenitor cell. Preferably, this time is about 72 hrs.

Preferably, tooth progenitor cell markers are as described herein. Preferably, such markers are assessed by in situ hybridisation.

Advantages

The present invention has a number of advantages. These advantages will be apparent in the following description.

By way of example, the present invention is advantageous since it requires minimum animal sacrifice.

Further, the present invention is advantageous since it is labour saving.

Further, the present invention is advantageous since it does not involve multiple surgical tissue recombination.

Tooth Development

Development of the mammalian tooth has been recognised as a model system for study of epithelial/mesenchymal interactions during organogenesis. Teeth start to develop early in mammalian embryogenesis (11 days in mice, 6 weeks in humans), from a series of reciprocal interactions between two cell types, oral epithelium and neural crest-derived mesenchyme cells.

Inductive signals for tooth development come from the epithelium whereupon the responding mesenchymal cells are programmed to become odontogenic (2). Odontogenic mesenchymal cells then provide instructive signals for further tooth development (3). The epithelial cells eventually give rise to ameloblasts which are responsible for enamel formation and mesenchyme cells form odontoblasts which produce dentine.

The identity of these different instructive signals has been revealed by gene expression studies and implantation experiments. FGF8, BMP4 and SHH are established as early instructive signals from the oral epithelium (3). BMP's, FGF's and activin are among the early signals from the mesenchyme (3,4).

Key molecules involved in tooth organogenesis signalling include Activin βA, which is expressed in presumptive tooth germ mesenchyme and is a signalling molecule in tooth development. Activin proteins are produced from two gene products, Activin βA and Activin βB which dimerise to form activin A (βA:βB), activin B (βB:βB) and activin AB (βA:βB). The closely related inhibins, inhibin A and inhibin B, are dimers consisting of an activin βA or βB subunit linked to an inhibin-specific α subunit (Vale et al., 1990; Roberts et al., 1991; Roberts and Barth, 1994).

Analysis of tooth development in Activin βA mutant embryos shows that incisor and mandibular molar teeth fail to develop beyond the bud stage. Activin βA is thus an essential component of tooth development, and is a mesenchymal cell marker gene.

Tooth Gene Expression Markers

Expression of well characterised mesenchymal and epithelial marker genes may be examined by any suitable method. For example, radioactive in situ hybridisation may be performed on embryos, such as up to the bud stage. Suitable genes to examine the expression patterns of may include Barx-1, Msx-1, Dlx-2, Pax-9, Gli-3, Lef-1, syndecan-1, Tgfβ-1, Tgfβ-3, Bmp-4, Bmp-7, Shh, CD44, Otlx-2, Lhx6, Lhx7, FGF8, Pitx2, or any other suitable marker gene. This is discussed in more detail below.

Mesenchymal Markers

Examples of such markers include Barx1, Dlx2, Dlx5, Msx1, Pax9, Activin Aβ, Lhx6, Lhx7 and others. These markers may be detected by any suitable means, such as western blotting, immunofluorescence, radioactive in situ hybridisation or other suitable means.

In wild type teeth at the bud stage Barx-1 gene expression is principally found in the molar region of the mandible and maxilla and is present in a broad field of neural crest derived mesenchymal cells rather than being restricted to dental mesenchyme (Ferguson et al., 1998. Tissier-Seta et al., 1995).

Msx-1, Lef-1 and Bmp-4 are expressed in the dental mesenchyme (i.e. the condensing mesenchymal cells associated with invaginating incisor and molar epithelial tooth buds) in response to epithelial signalling (Ferguson et al., 1998: Mackenzie et al., 1991; Kratochwil et al., 1996; Vainio et al., 1993).

Dlx-2 expression is principally found in mesenchymal cells immediately surrounding the epithelial bud, but is also present in the dental epithelium on the buccal side of the buds (Ferguson et al., 1998; Thomas et al., 1995; Qui et al., 1997).

Pax-9, Lhx6 and Lhx7 are expressed in early tooth mesenchyme prior to bud formation and subsequently in condensing mesenchyme at the bud stage (Ferguson et al., 1998; Neubuïser et al., 1997).

Gli-3 is expressed in the mesenchyme from E10.5. At the bud and cap stage Gli-3 expression is slightly more localised than Pax-9 expression, and is concentrated in the dental papilla and dental follicle (Ferguson et al., 1998; Hardcastle and Sharpe, 1998).

Syndecan-1, a cell surface heparin sulphate proteoglycan is transiently expressed in the dental mesenchyme and is thought to regulate dental mesenchymal cell condensation beneath the invaginating dental epithelium (Ferguson et al., 1998; Thesleff et al., 1996).

Tgfβ-1 is found in the dental mesenchyme and weakly in the epithelium of the incisors and only appears in the molars in the dental epithelium at the cap stage (Ferguson et al., 1998; Vaahtokari et al., 1991).

Tgfβ-3 expression is widespread in the mesenchyme of the face, but its expression appears to be substantially absent from the condensing mesenchymal cells immediately adjacent to the epithelial buds of incisors and molars (Ferguson et al., 1998; Chai et al., 1994).

Epithelial Markers

Examples of such markers include Pitx2, p21, Wnt7b and others. These markers may be detected by any suitable means, such as western blotting, immunofluorescence, radioactive in situ hybridisation or other suitable means.

Genes known to be expressed in tooth germ epithelium include Bmp-7, Sonic hedgehog (Shh), CD44, FGF8, Pitx2 and Otlx-2 genes.

In wild-type embryos, Bmp-7 is initially expressed in the dental epithelium, but expression shifts to the mesenchyme around the tooth buds from E13.5 (Åberg et al., 1997). At E13.5 mesenchymal Bmp-7 expression is found only in lower incisors, which are the most advanced developmentally at this stage, whereas expression persists in the epithelium of upper incisors and molars (Ferguson et al., 1998).

Shh is expressed in the epithelial thickening of early tooth germs and is thought to be an important component of the signals that pass from the epithelium to the underlying mesenchyme at this early stage, inducing gene expression in the mesenchyme and instructing it to begin condensation (Bitgood and McMahon, 1995; Thesleff and Sharpe, 1997). At later stages, Shh is down-regulated but transcripts reappear in the epithelial cells that constitute the enamel knot, a transient signalling centre that arises in the dental epithelium at the late bud stage of tooth development (Ferguson et al., 1998; Vaahtokari et al, 1996).

CD44 and Otlx-2 are expressed more widely in the oral epithelium than Shh (Ferguson et al., 1998; Mucchielli et al, 1997). CD44 encodes the hyaluronan receptor and Otlx-2 is the murine homologue of the human gene which when mutated, causes the disease known as Rieger syndrome in which teeth are absent (Semina et al; 1996).

Follistatin is an activin-binding protein that has been shown to inhibit the activity of activin (Michel et al., 1993; De Winter et al., 1996). The expression pattern of Follistatin may be examined by in situ hybridisation analysis (Ferguson et al., 1998). Follistatin expression is found in tooth germ epithelial cells immediately adjacent to activin βA expressing cells from E11.5. At later stages, follistatin transcripts are restricted to the columnar-shaped cells that form the outermost layer of the epithelial bud, while the central core of epithelial cells are follistatin-negative (Ferguson et al., 1998). Follistatin is therefore expressed in the tooth epithelium adjacent to and in a complementary pattern to activin βA in the tooth mesenchyme.

Tooth Primordia

Tooth primordia can be cultured in vitro allowing a variety of manipulation studies including introduction of genes and/or proteins and tissue recombinations. Most significantly, manipulated primordia can be transferred to renal capsules of adult animals (such as mice) to produce conditions for development of adult teeth. Advantageously, tooth progenitor cells according to the present invention may be used for the production of tooth primordia, or more fully developed teeth.

It is envisaged that a tissue engineering approach based on the teachings disclosed herein with respect to tooth development may be used to generate teeth in vitro and ultimately in vivo in an adult oral cavity.

ES Cells

As shown herein, cultured cells such as ES cells can replace neural crest-derived mesenchymal cells in production of tooth progenitor cells. Similarly, as disclosed herein, artificial epithelium may be engineered to emulate embryonic oral epithelium. It is envisaged that the cultured epithelial cells disclosed herein may be used in the production of artificial epithelium, and that this epithelium may be engineered to posess characteristics of oral epithelium, thereby allowing replacement of embryonic epithelium with engineered epithelium in the production of tooth progenitor cells.

Other sources of stem cells that may replace neural crest-derived mesenchymal cells may include primary adult neural stem cells. These may be obtained using established methods, for example as described in Johansson et al (Cell vol. 96, p25 (1999)) and/or Clarke et al. (Science vol. 288, p1660 (2000)). Such cells are even capable of forming neural crest cells when transplanted into mouse blastocysts. Cultured neural stem cell line(s) may also be used to replace neural crest-derived mesenchymal cells according to the methods of the present invention.

It is envisaged that the tooth progenitor cells according to the present invention may be usefully employed to generate murine teeth entirely from cultured cells, by combining ES cell aggregates with epithelium produced from immortalised cell lines and ES cells.

The ability of ES cells to form primitive ectoderm-like cell populations has been established (5,6). The combination of secreted signals necessary to induce odontogenesis in such cells may be provided by experimental manipulation of the cells, for example using the bead delivery system as described herein. Moreover, it is envisaged that the ES cell-derived ectoderm may advantageously replace odontogenic ectoderm once the direction of signalling has transferred to the odontogenic mesenchyme.

Stem Cell Culture for Tooth Formation

As explained herein, the present invention involves method(s) for the generation of a mesenchyme tissue capable of forming teeth from cultured stem cells. The stem cells may be prepared for the induction/interaction in a number of ways. For example, they may be pelleted to form small aggregates. This may be accomplished by pelleting them onto filters. Such filters may comprise any suitable substrate, such as pregelatinised Millipore filters. For convenience, the filters may be supported by metal grids, for example as described in Ferguson et al. (1998). The stem cells may be pelleted into small holes made in a gel or other suitable semi-solid support. The gel may be a collagen gel. The gel may be Collaborative Biomedical Products' Matrigel or a similar substrate. Epithelium is overlaid onto the stem cells to cover the hole which is them covered with a thin layer of gel and incubated. Gels used in this manner may themselves be supported by membrane(s) and/or metal grids as outlined above and in the Examples section.

Tooth Replacement

The present invention may be used for tooth replacement, particularly for human tooth replacement. For example, this would be accomplished using human ES cells in the methods of the current invention. It would be preferable to grow the tissue engineered teeth in the adult oral cavity, thereby allowing direct tooth replacement.

It is known that embryonic tooth primordia can develop and grow normally in the adult environment, for example using renal transfers (1,4). It seems that sites such as the adult kidney and eye provide a suitable environment largely by allowing an adequate blood supply. We therefore envisage that tooth rudiments surgically implanted into the oral cavity should develop normally.

In addition to being able to develop a series of procedures to allow tooth replacement it is desirable that the tooth that develops in situ is of the correct shape and size. A number of the genes that determine tooth shape are known, and by manipulation of these genes it is possible to change tooth shape (1,4,7,8). Similarly, it is shown experimentally that modulation of signalling events leads to alteration of tooth size.

For example, inhibition of Wnt signalling leads to the development of smaller teeth (9). These observations could be advantageously employed in the methods of the present invention.

The methods of the present invention could be usefully applied to a tissue engineering approach for the generation of a complete mammalian organ, a tooth, de novo from cultured cells. The approach involves the replacement of embryonic tissues that form teeth with tissues generated from cultured cells as disclosed herein.

One aspect of the present invention concerns embryonic oral epithelium, that when recombined with mesenchyme derived from cultured embryonic stem cells (ES cells) induces tooth specific gene expression and early tooth development in the ES cell tissue.

As is known in the art, the second branchial arch of mammalian embryos does not develop teeth. In one embodiment of the invention, using a double recombination technique with tissues derived from gentically marked mouse strains, odontogenesis is induced in second branchial arch mesenchyme. It is further demonstrated that this tissue is then able to induce odontogenesis in second branchial arch epithelium. Early stage tooth germs are then formed from these recombined tissues according to the present invention. Formation of said tooth germs is confirmed by monitoring expression of the appropriate molecular markers as described above. Thus, it is an advantageous feature of the present invention that non-odontogenic tissues can be made to form teeth as disclosed herein.

In another embodiment, the invention relates to the induction of ES cell-based mesenchyme to undergo odontogenesis. Oral epithelium is recombined with an embryonic stem cell mesenchyme. Epithelial invaginations (tooth buds) are formed. Using molecular markers for tooth buds, it is demonstrated that expression of these markers is induced in the ES cell mesenchyme around the epithelial invaginations, indicative of early odontogenesis taking place and confirming tooth bud formation.

Thus, it is an advantageous feature of the present invention that ES cell based mesenchyme can be induced to undergo odontogenesis.

Advantageously, the methods of the present invention may be employed to form teeth entirely from embryonic tissues that would not normally form teeth.

It is envisaged that the present invention may enable ES cells to replace neural crest-derived embryonic cells and permit tooth development.

Advantageously, epithelial cells may be produced from cell lines and be used as a replacement for oral epithelium in vitro.

The methods of the present invention may be advantageously applied to the replacement of the embryonic environment usually required for tooth development by an adult environment, such as via implantation of tooth progenitor cells or structures resulting therefrom into an adult jaw for development. Teeth produced/transplanted according to the present invention continue to grow and develop when implanted into the jaw bone, and become attached thereto.

It is envisaged that the present invention provides for cells to be directed to follow an odontogenic pathway in culture and subsequently develop into mature teeth when implanted into mammalian kidney and/or jaw.

It is an advantage of the present invention that successful tooth development can be produced from cultured cells.

It is demonstrated herein that odontogenic signals can be passed to mesenchymal and epithelial cells which normally do not form teeth by programming them in culture for subsequent tooth development according to the present invention.

It is an advantage of the present invention that mesenchymal cells can be programmed by exposure to odontogenic signals (eg. from oral epithelium) in culture to subsequently form teeth on implantation (eg. renal implantation, or implantation into jaw).

It is an advantage of the present invention that tooth primordia attach and develop successfully following implantation into the jaw.

It is envisaged that the present invention facilitates the replacement of oral epithelium with cultured cell line(s), and/or facilitates the replacement of epithelium with protein signals which may be advantageously applied as protein and/or as gene(s) encoding same, and/or facilitates use of stem cells such as neural stem cells and/or embryonic stem cells for the production of tissue engineered teeth.

EXAMPLES

The present invention will now be described by way of example, in which reference is made to:

In slightly more detail:

FIG. 1 shows a developing bud; and

FIG. 2 shows visualised expression of tooth progenitor marker genes.

General Methods

Experiments herein are carried out on murine embryo explants cultured using an established system (see for example Ferguson et al., 1998, et seq.). Recombinations are performed using established methods involving separation of epithelium and mesenchyme with Dispase (4). Histology involves cutting and staining wax sections and in situ hybridisation with gene markers utilises 35S RNA probes with different probes used on adjacent sections. Renal transfers are carried out in six week old male CD1 mice using a UK Home Office approved procedure, renal extracts are harvested over 10 to 16 days, decalcified in EDTA, serial sectioned and stained. Organ/tissue culture is according to methods known in the art, for example in ('Organ culture in the analysis of tissue interactions.' I.Thesleff and C.Sahlberg, from Molecular Embryology Methods and Protocols Vol. 97. Ch. 3, Ed.s P T Sharpe and I Mason; Humana Press 1999). ES cells are propagated, maintained and prepared according to standard protocols, which may be found for example in ('CRE recombinase mediated alterations of the mouse genome using embryonic stem cells.' Hadjantonakis et al., from Molecular Embryology Methods and Protocols Vol. 97. Ch.8, Ed.s P T Sharpe and I Mason; Humana Press 1999). Where appropriate, ES cells may be pelleted onto filters, or preferably are grown on pregelatinised filters using standard culture conditions as explained above.

Example 1

Tooth Development from Non-Odontogenic Embryonic Tissues

The extent to which teeth can develop from recombinations of embryonic tissues that do not normally form teeth is determined.

Oral epithelium (first branchial arch) from E10 embryos is recombined with mesenchyme from the second branchial arch. These explants are cultured for three days to initiate odontogenesis in the mesenchyme which is confirmed by in situ hybridisation with molecular markers.

Epithelial-Mesenchymal Tissue Recombinations

Recombinations are carried out at E11.5 and E13.5. Molar anlagen of the mandibles are dissected out in DMEM with glutamax-1. The epithelium and mesenchyme are isolated following incubation in a solution of Dispase (Gibco BRL) made up in calcium and magnesium free PBS at 2 units per ml for 10-15 minutes at 37° C. After incubation the mandibles are washed in D-MEM with 10% foetal calf serum (FCS), and the tissues are mechanically separated using fine tungsten needles. For recombination, epithelium and mesenchyme are aligned in the correct orientation (as taught in Ferguson et al., 1998) on top of transparent Nuclepore membrane filters (0.1 micron pore diameter; Costar). The recombinations are cultured for 24 to 48 hrs in D-MEM with 10% foetal calf serum, after which they are either fixed and processed for radioactive in situ hybridisation, or transplanted under the kidney capsule of male adult mice and cultured for a further 10 days to allow for full development of teeth.

In Situ Hybridisation

Radioactive in situ hybridisation procedures are carried out on embryos at E10.5-E14.5 as described by Wilkinson (1995). The radioactive antisense probes are generated from mouse cDNA clones such as activin βA, follistatin, Barx-1, Bmp-4, Bmp-7, CD44, Dlx-2, Fgf8, Gli-3, Otlx-2, Pax-9, Shh, Syndecan-1, Tgfβ-1, Tgfβ-3, or others as discussed herein.

After three days the oral epithelium is removed and replaced with second branchial arch epithelium. At this time odontogenic potential resides in the second branchial arch mesenchyme (having been induced by the oral epithelium) which then provides the inductive signals back to the second branchial arch epithelium. Explants are cultured for a further three days and assayed for formation of tooth buds by histology and molecular markers.

Figure 1:
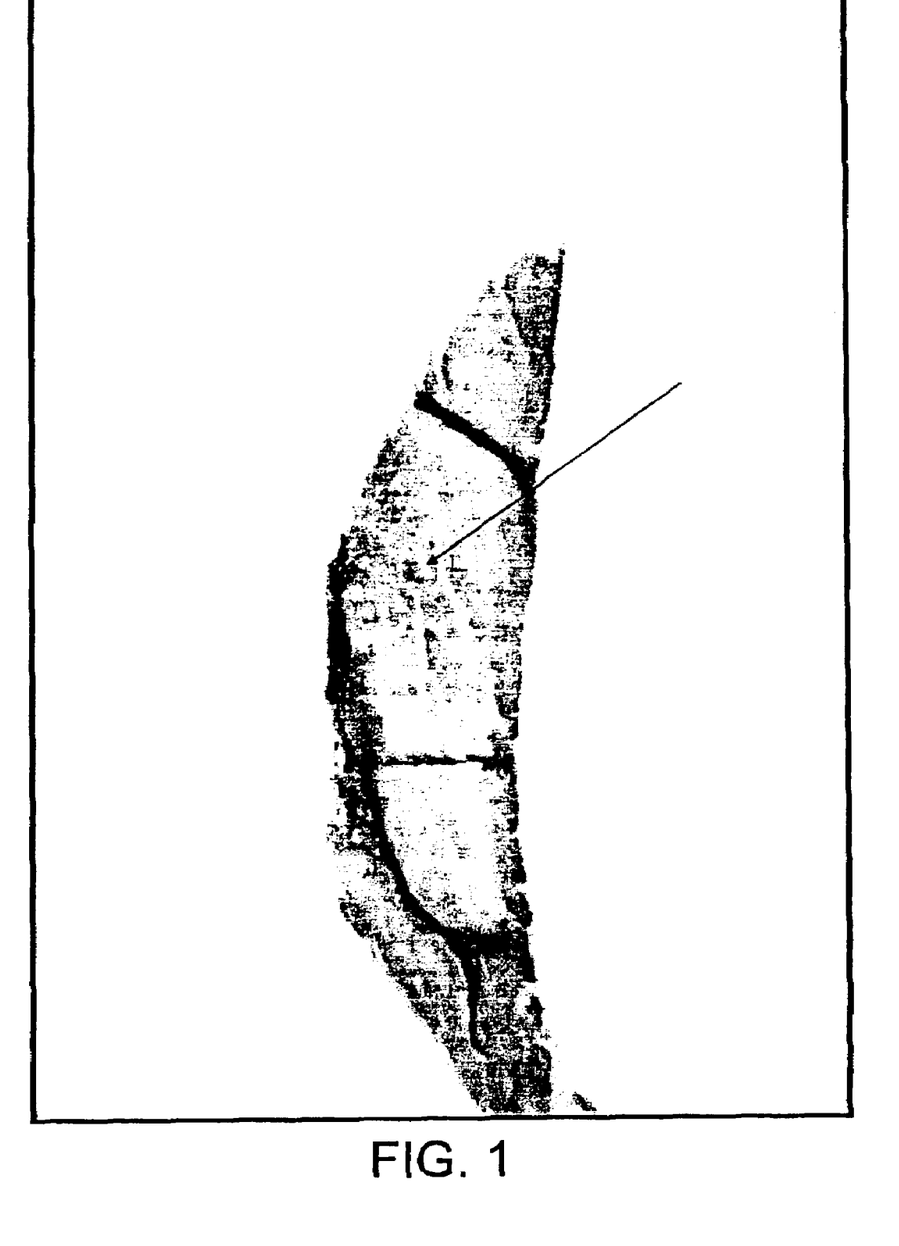
FIG. 1 which shows a stained section.

FIG. 1 shows formation of tooth buds in this system (arrowed).

Identical explants are transferred to renal capsules to demonstrate that normal teeth can form from a combination of second branchial arch tissues that can not normally form teeth. It is important in these experiments to ensure that there is no contamination of second branchial arch tissues with first arch cells. This is monitored by using separate embryos from ROSA 26 and GFP mice, whose cells may be easily distinguished using the engineered markers therein. By harvesting first arch tissues from GFP mice and second arch tissues from ROSA 26 mice the origins of all cells in the teeth formed can be assayed by Lac Z staining and GFP detection.

Induction of Tooth Primordia from Mesenchymal Tissue

In vitro induction of tooth primordia from mesenchymal tissue is demonstrated. The the necessary signals are provided artificially using protein soaked beads. These tooth progenitors are then allowed to develop into fully grown teeth in vivo in adult animals.

Mandibles from embryos at E11.5, E12.5 and E13.5 are dissected in D-MEM with glutamax-1 (Gibco BRL). The rest of the embryo is used for genotyping. For cultures at E11.5 and E13.5, individual molar tooth anlagen are isolated from surrounding oral and aboral tissue, while for cultures at E12.5, whole mandibles are used. These are placed with oral surfaces facing upwards, on membrane filters supported by metal grids following the Trowell technique as modified by Saxen (Trowell, 1959; Saxen, 1966). Affi-Gel agarose beads (BioRad) are washed several times in PBS then are dried out before being added to recombinant activin A protein at 1 mg/ml, a concentration known to be able to induce mesoderm formation in *Xenopus* animal cap assays (Ferguson et al., 1998), or BSA at the same concentration for one hour at 37° C. The beads are pushed into the mesenchyme so that they lay in close proximity to the developing tooth germs. The mandible explants at E11.5 and E13.5 are cultured with beads for 24 to 72 hrs in D-MEM with 10% foetal calf serum. The E12.5 mandible explants are cultured with beads for 6 days, then fixed in 4% paraformaldehyde (SIGMA) and processed for histological examination using haemotoxylin/eosin staining. A standard incubator is used at 37° C. with an atmosphere of 5% $CO_2$ in air and 100% humidity. All solutions contain penicillin and streptomycin at 20 IU/ml. After the period of culture, the E11.5 and E13.5 explants are removed from their membrane filters and transplanted under the kidney capsules of male adult mice. During this procedure, most of the beads are dissociated from the explants. The explants are cultured in host kidneys for 10 days to allow for full development of teeth. The resulting tissues are then fixed in Bouin's solution (SIGMA), dehydrated, and embedded. Serial sections of 7 microns are cut and stained using alcian blue/chlorontine fast red.

Induction of Tooth Progenitor Cells Using Artificial Fgf-8/Bmp-4 Signals

Mandibles are dissected at E11.5. Where indicated, epithelium is removed after incubation in Dispase (2 units per ml) for 10 minutes at 37° C. For the application of Fgf8 protein, heparin acrylic beads (Sigma) are washed and then incubated overnight in 1 mg/ml Fgf-8 protein (recombinant mouse FGF-8b; R&D Systems, Europe) at 4° C. For the application of Bmp-4 protein, Affi-Gel agarose beads are washed and soaked in the protein (recombinant human BMP-4) for 1 hr at 37° C. A concentration of 100 μg/μl Bmp-4 was used, since this concentration has been shown to inhibit Pax-9 expression in a similar assay (Neubüser et al, 1997). After 24-48 hrs in culture the explants are fixed and processed for in situ hybridisation. Digoxygenin wholemount in situ hybridisation is carried out as described by Pownall et al (1996).

Example 2

Use of Cultured Cells in the Production of Tooth Progenitor Cells

Replacement of neural crest-derived mesenchymal cells with ES cells, and subsequent determination of these as tooth progenitor cells is demonstrated.

Disclosed herein is a way of reproducibly producing a solid mesenchymal tissue from cultured cells such as ES cells, said tissue being capable of interacting with oral epithelium and forming teeth.

Figure 2:
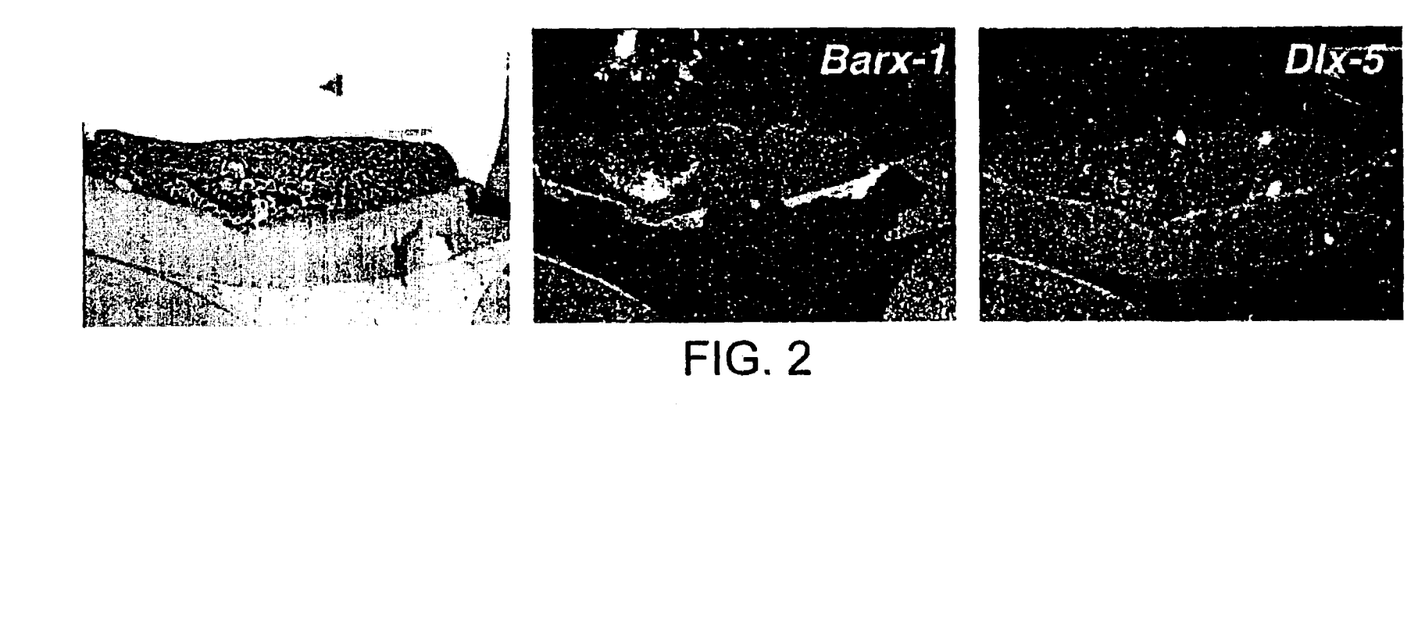
FIG. 2 which shows a stained section.

In order to establish that ES cells can be used to replace neural crest-derived mesenchymal cells, mouse ES cells are pelleted onto filters to form small aggregates. These aggregates are overlaid with oral epithelium from E10 mouse embryos and allowed to develop for three days in culture. Histology of the cultures reveals evidence of epithelial invaginations with surrounding expression of the tooth mesenchymal marker genes Barx1 and Dlx5 as shown in FIG. 2.

Wild type 129 ES cells are grown and maintained in a pluripotent state using the same conditions as are routinely used for gene targeting. Cells are pelleted onto pre-gelatinised Millipore filters and allowed to grow for 1 to 3 days to form aggregates. ES cell aggregates are overlaid with E10 oral epithelium from ROSA 26 embryos and cultured for three to five days. Histology, molecular markers and renal transfer analysis are carried out as described herein. As a control, ES cells homozygous for a targeted allele of Msx1 will be used. Msx1 +/− ES and −/− cells are produced by re-electroporation of +/− ES cells with the original targeting construct followed by selection with a higher concentration of G418. Since Msx1 −/− embryos do not develop teeth, −/− ES cells do not permit tooth development beyond the bud stage when recombined with oral epithelium (10).

Furthermore, the protocol outlined in Example 1 above may be followed where, after induction of odontogenic potential in the ES cell tissue, the oral epithelium is replaced by non-odontogenic second branchial arch epithelium.

Example 3

Use of Cultured Cells in the Formation of Oral Epithelium.

The replacement of oral epithelium with odontogenic epithelial cultured cell lines is demonstrated.

It is taught herein how to replace oral epithelium with an epithelium derived from immortalised lines of tooth epithelial cells. Firstly, a number of clonal lines of immortalised cells derived from early odontogenic epithelium are generated.

Epithelial Cultures

Oral epithelium is isolated after incubation of E11.5 mandibles in Dispase (2 units per ml) for 10 minutes at 37° C. The epithelium is cultured in Matrigel (Collaborative Biomedical Products) on membrane filters supported by metal grids as described in (Ferguson et al., 1998). Matrigel is a solubilised basement membrane extracted from the Engelbreth-Holm-Swarm mouse sarcoma cell line and provides a matrix within which epithelial cells can develop. The gel sets rapidly and irreversibly at temperatures between 22° C. to 35° C. Therefore, the product is kept on ice and pre-cooled pipettes used. The filters are covered with Matrigel which is left to set at 37° C. before the epithelia are pipetted on top. To visualise the epithelia they are weakly dyed with neutral red before being placed onto the Matrigel. Affi-Gel agarose beads (BioRad) soaked in recombinant activin A protein (1 mg/ml) or BSA are prepared as described herein. Beads are placed on top of the epithelia, which are then topped with more Matrigel so that the cultures are surrounded. The epithelia with beads are cultured for 48 hrs in D-MEM with 10% foetal calf serum. After the period of culture, cultures are washed in ice-cold methanol for 1 minute and then fixed in fresh 4% paraformaldehyde for 1 hour at RT. Cultures are then prepared for $^{35}S$ section in situ hybridisation.

Immortalised lines of odontogenic epithelial cells are produced. The cell lines generated are tested for their odontogenic inductive capacities. Lines are established that express amelogenins, unique tooth specific proteins involved in enamel formation. Molecular markers are analysed to determine whether the signalling properties of early oral epithelium are well established.

Cells that have properties of ameloblasts are identified by screening the lines for amelogenin expression. RTPCR is used to screen for expression of FGF8, BMP4, SHH and Pitx2 (the earliest marker of oral epithelium) to determine which lines are likely to be able to replace oral ectoderm.

To test the odontogenic inducing capacity of cell lines, mesenchymal explants (epithelium removed) from mandibular primordia of E12 embryos are cultured on filters in small wells in collagen gels. Cultured cells from the screened lines are layered onto the mesenchymal explants and the explants cultured for 3 days. The extent of epithelium formation and invagination is assayed histologically and with tooth molecular markers.

Since at E11.5 odontogenic inducing capacity resides in the mesenchyme, naïve epithelium responds to these signals and allows tooth development. If the growth medium used in the cultures does not contain the factors required for the cells lines to produce an odontogenic epithelium, conditioned media from cultures of intact mandibular primordia explants are used.

The immortalised cell lines' inductive odontogenic properties are assayed by following the methods of the above examples, but replacing mandibular primordia mesenchyme with second branchial arch mesenchyme.

If the epithelial cells do not properly induce odontogenesis, the expression of inductive signalling molecules (FGF8, BMP4, SHH etc.) is assayed in the collagen explant cultures and any missing signals are replaced either by purified proteins on beads or by electroporation of gene expression constructs (see below).

Example 4

Engineering Artificial Epithelium

As disclosed herein, oral epithelial inductive signals may be supplied using purified proteins. The following experimental approaches are used to reproduce (replace) inductive signals in oral epithelium produced from immortalised cultured cells/ES cells.

A number of signalling proteins have been identified that are secreted by oral epithelium that direct mesenchymal cells to become odontogenic and generate epithelial tooth buds. These signals include FGF8, BMP4 and SHH (3,11). These factors may be sufficient to induce tooth initiation in non-odontogenic cells.

The feasibility of engineering an artificial oral epithelium is tested. Beads soaked in a combination of signalling proteins involved in initiation are implanted into the epithelium of second branchial arch extracts and tooth development analysed.

Teeth do not develop on the second branchial arch and so any evidence of tooth development following addition of exogenous signals implicates initiation. A range of concentrations and combinations are tested.

Structures are formed in the explants treated with factors that are not formed in control explants.

Alternatively, electroporation may be used to transfer gene expression constructs into localised epithelial sites to reproduce the first brachial arch spatial arrangements of these three signalling molecules in the second branchial arch.

Example 5

Production of ES Cell Derived Epithelium

In the production of tooth progenitor cells according to the present invention, it is desirable that oral epithelium be replaced by an ES cell-derived (ie. cultured cell-derived) epithelium.

The generation of animal tooth progenitors such as human tooth progenitors will preferably be accomplished entirely from cultured cells. A convenient source of human cells is cultured ES cells. The ability of ES cells to replace oral epithelium is demonstrated.

ES cells have been shown to be capable of forming ectoderm/epithelial cells and following similar lines to those described above for immortalised epithelial cell lines, the requirements for ES cells to generate an inductive odontogenic epithelium are investigated.

For control ES cells Pitx2 –/– ES cells are used since Pitx2 is expressed in early oral epithelium and Pitx2 –/– embryos fail to form cap stage tooth buds (12,13,14).

Preferably, both odontogenic epithelium and mesenchyme are replaced with ES generated epithelium and mesenchyme in a single explant in the methods of the above examples.

Example 6

Development of Tooth Explants in the Oral Cavity

Tooth explants can develop normally in at least two adult sites, the renal capsule and anterior chamber of the eye. It is determined whether explants may develop in the adult oral cavity.

Adult male mice are anaesthetised and single first molar teeth extracted. Molar tooth primordia explants cultured for 3 days as in the above examples are transplanted into the extraction site. The oral mucosa are closed over the explant, sutured and left for 10-16 days to develop during which time the animal is fed a soft diet.

The extent of explanted tooth development is assayed by histology. These experiments require the use of microsurgery. Surgical expertise is first acquired on sacrificed mice before being carried out on live animals.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

Åberg, T., Wozney, J. and Thesleff, I. 1997. Expression patterns of BMPs in the developing mouse tooth suggest roles in morphogenesis and cell differentiation. *Dev. Dyn.* 210: 383-396.

Asashima, M., Nakano, H., Shimada, K., Kinoshita, K., Ishii, K., Shibai, H., and Ueno, N. 1990. Mesodermal induction in early amphibian embryos by activin A (erythroid differentiation factor). *Roux's Arch. Dev. Biol.* 198: 330-335.

Bitgood. M. J. & McMahon, A. P. 1995. Hedgehog and Bmp genes are coexpressed at many diverse sites of cell-cell interaction in the mouse embryo. *Dev. Biol.* 172: 126-138.

Chai, Y., Mah, A., Crohin. C., Groff, S., Bringas, P., Jr., Le, T., Santos, V. and Slavkin, H. C. 1994. Specific transforming growth factor-beta subtypes regulate embryonic mouse Meckel's cartilage and tooth development. *Dev. Biol.* 162: 85-103.

Chen, Y., Bei, M., Woo, I., Satokata, I. and Maas, R. 1996. Msx1 controls inductive signalling in mammalian tooth morphogenesis. *Development* 122: 3035-3044.

Conlon, F. 1994. A primary requirement for Nodal in the formation and maintenance of the primitive streak in the mouse. *Development* 120: 1919-1928.

Crossley, P. H. and Martin, G. R. 1995. The mouse Fgf8 gene encodes a family of polypeptides and is expressed in regions that direct outgrowth and patterning in the developing embryo. *Development* 121, 439-451.

De Winter, J. P., Ten Dijke P., De Vries, C. J. M., Van Acterberg, T. A. E., De Waele, P., Huylebroeck, D., Verschueren, K. and Van den Eijnden-van Raaij, A. J. M. 1996. Follistatins neutralise activin bioactivity by inhibition of activin binding to its type II receptors. *Mol. Cell Endocrinol.* 116: 105-114.

Dohrmann, C. E., Hemmati-Brivanlou, A., Thomsen, G. H. and Fields, A. 1993. Expression of activin mRNA during early development in *Xenopus laevis*. *Dev. Biol.* 157: 474-183.

Dyson, S. and Gurdon, J. B. 1997. Activin signalling has a necessary function in *Xenopus* early development. *Curr. Biol.* 7: 81-84.

Fainsod, A., Deissler, K., Yelin, R., Marom, K., Epstein, M., Pillemer, G., Steinbeisser, H. and Blum, M. 1997. The dorsalizing and neural inducing gene follistatin is an antagonist of BMP-4. *Mech. Dev.* 63: 39-50.

Feijen, A., Goumans, M. J. and van den Eijnden-van Raaij. 1994. Expression of activin subunits, activin receptors and follistatin in postimplantation mouse embryos suggests specific developmental functions for different activins. *Development* 120: 3621-3637.

Ferguson C. A., Tucker A. S., Christiensen L., Lau A. L., Matzuk M. M. and Sharpe P. T. 1998. Activin is an essential early mesenchymal signal in tooth development that is required for patterning of the murine dentition. *Genes Dev.* 12:2636-2649

Green, J. B. A., and Smith J. C. 1990. Graded changes in dose of a *Xenopus* activin A homologue elicit stepwise transitions in embryonic cell fate. *Nature* 347: 391-394.

Green, J. B. C., New, H. V., and Smith, J. C. 1992. Responses of embryonic *Xenopus* cells to activin and FGF are separated by multiple dose thresholds and correspond to distinct axes of the mesoderm. *Cell* 71: 731-739.

Grigoriou, M., Tucker, A. S., Sharpe, P. T. and Pachnis, V. 1998. Expression and regulation of Lhx6 and Lhx7, a novel subfamily of LIM homeodomain encoding genes, suggests a role in mammalian head development. *Development*, in press.

Hardcastle, Z., Mo, R., Nui, C.-c. and Sharpe, P. T. 1998. The Shh signalling pathway in tooth development: defects in Gli2 and Gli3 mutants. *Development*. In press.

Heikinheimo, K., Begue-Kim, C., Ritvos, O., Tuuri, T. and Ruch, J. V. 1997. The activin-binding protein follistatin is expressed in developing murine molar and induces odontoblast-like cell differentiation in vitro. *J. Dent. Res.* 76: 1625-1636.

Heikinheimo, M., Lawshe, A., Shackleford, G. M., Wilson, D. B. and MacArthur, C. A. 1994. Fgf-8 expression in the post-gastrulation mouse suggests roles in the development of the face, limbs and central nervous system. *Mech. Dev.* 48: 129-138.

Hemmati-Brivanlou, A., and Melton, D. A. 1992. A truncated activin receptor dominantly inhibits mesoderm induction and formation of axial structures in *Xenopus* embryos. *Nature* 359: 609-614.

Hemmati-Brivanlou, A., and Melton, D. A. 1994. Inhibition of activin receptor signalling promotes neuralization in *Xenopus*. *Cell* 77: 273-281.

Hemmati-Brivanlou, A., Kelly, O. G., and Melton, D. A. 1994. Follistatin, an antagonist of activin, is expressed in the Spemann Organiser and displays direct neuralizing activity. *Cell* 77: 283-295.

Iseki, S., Araga, A., Ohuchi, H., Nohno, T., Yoshioka, H., Hayashi, F. and Noji, S. 1996. Sonic hedgehog is expressed in epithelial cells during development of whisker, hair, and tooth. *Biochem. Biophys. Res. Commun.* 218: 688-693.

Kettunen, P. and Thesleff, I. 1998. Expression and function of FGFs-4, -8, and -9 suggest functional redundancy and repetitive use as epithelial signals during tooth morphogenesis. *Dev. Dyn.* 211: 256-268.

Kollar, E. J. and Baird G. R. 1969. The influence of the dental papilla on the development of tooth shape in embryonic mouse tooth germs. *J. Embryol. Exp. Morph.* 21: 131-148.

Kratochwil, K., Dull, M., Fari-as, I., Galceran, J. and Grosschedl, R. 1996. Lef1 expression is activated by BMP-4 and regulates inductive tissue interactions in tooth and hair development. *Genes Dev.* 10: 1382-1394.

Lumsden A G. 1988. Spatial organisation of the epithelium and the role of neural crest cells in the initiation of the mammalian tooth germ. *Development* 103: 155-169.

Mackenzie, A., Leeming, G. L., Jowett. A. K., Ferguson, M. W. J. and Sharpe, P. T. 1991. The homeobox gene Hox-7.1 has specific regional and temporal expression patterns during early murine craniofacial embryogenesis, especially tooth development in vivo and in vitro. *Development* 111: 269-285.

Matzuk, M. M., Kumar, T. R., Vassalli, A., Bickenbach, J. R., Roop, D. R., Jaenisch, R. and Bradley, A. 1995a. Functional analysis of activins during mammalian development. *Nature* 374: 354-356.

Matzuk, M. M., Kumar, and Bradley, A. 1995b. Different phenotypes for mice deficient in either activins or activin receptor type II. *Nature* 374: 356-360.

Matzuk, M. M., Lu, N., Vogel, H., Selheyer, K., Roop, D. R., and Bradley, A. 1995c. Multiple defects and perinatal death in mice deficient in follistatin. *Nature* 374: 360-363.

Michel, U., Farnworth, P. and Finlay, J. P. 1993. Follistatins: more than follicle-stimulating hormone suppressing proteins. *Mol. Cell Endocrinol.* 91: 1-11.

Mina M., and Kollar E. J. 1987. The induction of odontogenesis in non-dental mesenchyme combined with early murine mandibular arch epithelium. *Arch. Oral. Biol.* 32: 123-127.

Mucchielli, M., Mitsiadis, T. A., Raffo, S., Brunet, J., Proust, J. and Goridis, C. (1997) Mouse Otlx2/RIEG expression in the odontogenic epithelium precedes tooth iniation and requires mesenchymal derived signals for its maintenance. *Dev. Biol.* 189:275-284.

Nakamura. T., Takio, K., Eto, Y., Shibai, H., Titani, K. and Sugino, H. 1990. Activin-binding protein from rat ovary is follistatin. *Science* 247: 836-838.

Neubüser, A., Peters, H., Balling, R. and Martin, G. R. 1997. Antagonistic interactions between FGF and BMP signalling pathways: a mechanism for positioning the sites of tooth formation. *Cell.* 90: 247-255.

Page, K. M. 1990. Bone. *In Theory and Practice of Histological techniques. Third Edition.* (ed J. D. Bancroft and A. Stevens), pp. 309-341. Churchill Livingstone, Edinburgh, London, Melbourne and New York.

Pownall, M. E., Tucker, A. S., Slack, J. M. W. and Isaacs, H. V. 1996. eFGF, Xcad3 and Hox genes form a molecular pathway that establishes the anteroposterior axis in *Xenopus. Development* 122: 3881-3892.

Qiu, M., Bufone, A., Ghattas, I., Menses, J. J., Sharpe, P. T., Presley, R., Pedersen, R. A. & Rubenstein, J. L. R. 1997. Role of Dlx-1 and -2 in proximodistal patterning of the branchial arches: mutations alter morphogenesis of proximal skeletal elements derived from the first and second branchial arches. *Dev. Biol.* 185: 165-184.

Roberts, V. J. and Barth, S. L. 1994. Expression of messenger ribonucleic acids encoding the inhibin/activin system during mid- and late-gestation rat embryogenesis. *Endocrinology* 128: 914-923.

Roberts, V. J., Sawchenko, P. E. and Vale, W. W. 1991. Expression of inhibin/activin subunit messenger ribonucleic acids during rat embryogenesis. *Endocrinology* 128: 3122-3129.

Saxen, L. 1966. The effect of tetracyclin on osteogenesis in vitro. *J. Exp. Zool.* 162: 269-294.

Satokata, I. & Maas, R. 1994. Msx-1 deficient mice exhibit cleft palate and abnormalities of craniofacial and tooth development. *Nature Genet.* 6: 348-356.

Semina, E. V., Reiter, R., Leysens, N. J., Alward, W. L., Small, K. W., Datson, N. A., Siegel-Bartelt, J., Bierke-Nelson, D., Bitoun, P., Zabel, B. U., Carey, J. C. and Murray, J. C. 1996. Cloning and characterization of a novel bicoid-related homeobox transcription factor gene, RIEG, involved in Rieger syndrome. *Nat. Genet.* 14: 392-399.

Thesleff, I. and Sharpe, P. T. 1997. Signalling networks regulating dental development. *Mech. Dev.* 67: 111-123.

Thesleff, I, Vaahtokari, A, & Partanen, A-M. 1995. Regulation of organogenesis. Common molecular mechanisms regulating the development of teeth and other organs. *Int. J. Dev. Biol.* 39: 35-50.

Thesleff, I., Vaahtokari, A., Vainio, S. and Jowett, A. 1996. Molecular mechanisms of cell and tissue interactions during early tooth development. *Anatomical Record* 245: 151-161.

Thomas, B. T., Porteus, M. H., Rubenstein, J. L. R. and Sharpe, P. T. 1995. The spatial localisation of Dlx-2 during tooth development. *Conn. Tiss. Res.* 32: 27-34.

Thomas, B. L., Tucker, A. S., Qui, M., Ferguson, C. A., Hardcastle, Z., Rubenstein, J. L. R. and Sharpe, P. T. 1997. Role of Dlx-1 and Dlx-2 genes in patterning of the murine dentition. *Development* 124: 4811-4818.

Thomsen, G., Woolf, T., Whitman, M., Sokol, S., Vaughan, J., Vale, W., and Melton, D. A. 1990. Activins are expressed early in *Xenopus* embryogenesis and can induce axial mesoderm and anterior structures. *Cell* 63: 485-193.

Tissier-Seta, J. P., Mucchielli, M. L., Mark, M., Mattei, M. G., Goridis, C. and Brunet, J. F. 1995. Barx1, a new mouse homeodomain transcription factor expressed in cranio-facial ectomesenchyme and the stomach. *Mech. Dev.* 51: 3-15.

Trowell, O. A. 1959. The culture of mature organs in a synthetic medium. *Exp. Cell Research* 16: 118-147.

Vaahtokari, A., Vainio, S. and Thesleff, I. 1991. Associations between transforming growth factor beta 1 RNA expression and epithelial-mesenchymal interactions during tooth morphogenesis. *Development* 113: 985-994.

Vaahtokari, A., Åberg, T., Jernvall, J., Keranen, S. and Thesleff, I. 1996 The enamel knot as a signalling center in the developing mouse tooth. *Mech. Dev.* 54: 39-43.

Vainio, S., Karavanova, I., Jowett, A. and Thesleff, I. 1993. Identification of BMP-4 as a signal mediating secondary induction between epithelial and mesenchymal tissues during early tooth development. *Cell* 75: 45-58.

Vale, W. W., Hseuh, A, Rivier, C. and Yu, J. 1990. The inhibin/ activin family of hormones and growth factors. In: *Peptide growth factors and their receptors II.* (ed M. B. Sporn and A. B. Roberts), pp. 211-248. Springer-Verlag, Berlin.

van Genderen, C., Okamura, R. M., Fari-as, I., Quo, R. G., Parslow, T. G., Bruhn, L. and Grosschedl, R. 1994. Development of several organs that require inductive epithelial-mesenchymal interactions is impaired in LEF-1-deficient mice. *Genes Dev.* 8: 2691-2703.

Wilkinson, D. G. 1995. In Situ Hybridisation, A practical approach. IRL Press, Oxford, UK.

Yamashita, H., ten Dijke, P., Huylebroeck, D., Sampath, T. K., Andries, M., Smith, J. C., Heldin, C.-H. and Miyazono, K. 1995. Osteogenic protein-1 binds to activin type II receptors and induces certain activin-like effects. *J. Cell. Biol.* 130: 217-226.

NUMBERED REFERENCES

1. Tucker A S, Matthews K L and Sharpe P T. (1998). Science 282, 1136-1138
2. Lumsden A S G (1988) Development 103, 122-169
3. Thesleff I and Sharpe P T (1997) Mechs. Dev. 67, 111-123
4. Ferguson C A, Tucker A S, Christensen L, Lau A L, Matsuk M M and Sharpe P T (1998) Genes Dev. 12, 2636-2649
5. Bagutti C, Wobus A M, Fassler R and Watt F M (1996) Dev. Biol. 179, 184-196
6. Rathjen J, Lake J-A, Bettess M D, Washington J M, Chapmen G and Rathjen P D (1999) J. Cell Sci. 112, 601-612
7. Thomas B L, Tucker A S, Qiu M, Ferguson C A, Hardcastle Z, Rubenstein J L R and Sharpe P T (1997). Development 124, 4811-4818
8. Ferguson C, Tucker A S and Sharpe P T (2000) Development in press.
9. Sarkar L and Sharpe P T (2000) J Dent. Res. in press.
10. Satokata I and Maas R (1994) Nat. Gen. 6, 348-356
11. Hardcastle, Z, Mo, R., Hui, C-c and Sharpe P. T. (1998) Development 125, 2803-2811
12. Lu M-F, Pressman C, Dyer R, Johnson R and Martin J F (1999) Nature 401, 276-278
13. Lin C R, Kioussi C, O'Connell S, Briata P, Szeto D, Liu F, Izpisua-Belmonte J C and Rosenfeld M G (1999) Nature 401, 279-282
14. Gage P J, Suh H and Camper S A (1999) Development 126, 4643-1651

The invention claimed is:

1. A method for producing a tooth progenitor cell from a) a cultured human or mouse embryonic stem cell, or b) a human or mouse neural stem cell comprising the steps of:
   a) providing a cultured human or mouse embryonic stem cell or the human or mouse neural stem cell,
   b) contacting the stem cell with an oral epithelial cell,
   c) incubating the contacted stem cell of step b) with the oral epithelial cell for a time sufficient to produce a tooth progenitor cell,
   wherein the tooth progenitor cell co-expresses Barx-1 and Dlx-5, and
   wherein the tooth progenitor cell further expresses a combination of tooth gene expression markers capable of specifically identifying the tooth progenitor cell.

2. The method of claim 1, wherein the combination of tooth gene expression markers capable of specifically identifying the tooth progenitor cell comprises:
   a) a first tooth gene expression marker selected from the group consisting of Pax-9, Msx-1 and combinations thereof, and
   b) a second tooth gene expression marker selected from the group consisting of Lhx-6, Lhx-7 and combinations thereof.

3. The method of claim 1 wherein the combination of tooth gene expression markers capable of specifically identifying the tooth progenitor cell comprises:
   a) Msx-1, Lhx-7 and Pax-9, or
   b) Lhx-6 and Pax-9.

4. The method of claim 1 wherein the combination of tooth gene expression markers capable of specifically identifying the tooth progenitor cell comprises Msx-1, Lhx-7 and Pax-9.

5. A method for inducing differentiation of a cultured human or mouse embryonic stem cell, or b) a human or mouse neural stem cell, the method comprising the steps of:
   a) providing a cultured human or mouse embryonic stem cell or a human or mouse neural stem cell,
   b) contacting the stem cell with an oral epithelial cell,
   c) incubating the contacted stem cell of step b) with the oral epithelial cell for a time sufficient to induce differentiation of the stem cell,
   wherein the stem cell differentiation comprises the co-expression of Barx-1 and Dlx-5.

* * * * *